US007616110B2

(12) United States Patent
Crump et al.

(10) Patent No.: US 7,616,110 B2
(45) Date of Patent: Nov. 10, 2009

(54) MOBILE WIRELESS CUSTOMIZABLE HEALTH AND CONDITION MONITOR

(75) Inventors: Cindy Crump, Lovettsville, VA (US); Patrick Farrell, Falls Church, VA (US); Bruce Wilson, Williamsburg, VA (US)

(73) Assignee: AFrame Digital, Inc., Lovettsville, VA (US)

( * ) Notice: Subject to any disclaimer, the term of this patent is extended or adjusted under 35 U.S.C. 154(b) by 447 days.

(21) Appl. No.: 11/371,071

(22) Filed: Mar. 9, 2006

(65) Prior Publication Data

US 2006/0202816 A1 Sep. 14, 2006

Related U.S. Application Data

(60) Provisional application No. 60/660,342, filed on Mar. 11, 2005.

(51) Int. Cl.
*G08B 1/08* (2006.01)
*A61B 5/00* (2006.01)

(52) U.S. Cl. .............................. 340/539.11; 340/539.12; 340/531; 600/300; 600/301; 128/903; 702/19

(58) Field of Classification Search ............ 340/539.11, 340/539.12; 600/301
See application file for complete search history.

(56) References Cited

U.S. PATENT DOCUMENTS

| 5,416,695 | A | 5/1995 | Stutman et al. |
| 5,441,047 | A | 8/1995 | David et al. |
| 5,515,858 | A | 5/1996 | Myllymaki |
| 5,544,649 | A | 8/1996 | David et al. |
| 5,576,952 | A | 11/1996 | Stutman et al. |
| 5,897,493 | A | 4/1999 | Brown |
| 5,997,476 | A | 12/1999 | Brown |
| 6,050,940 | A | 4/2000 | Braun et al. |
| 6,126,595 | A | 10/2000 | Amano et al. |
| 6,198,394 | B1 | 3/2001 | Jacobsen et al. |
| 6,224,548 | B1 | 5/2001 | Gopinathan et al. |
| 6,248,064 | B1 | 6/2001 | Gopinathan et al. |
| 6,252,883 | B1 * | 6/2001 | Schweickart et al. ........ 370/441 |
| 6,292,698 | B1 * | 9/2001 | Duffin et al. .................. 607/32 |
| 6,307,481 | B1 | 10/2001 | Lehrman et al. |
| 6,336,900 | B1 | 1/2002 | Alleckson et al. |
| 6,368,273 | B1 | 4/2002 | Brown |
| 6,375,614 | B1 | 4/2002 | Braun et al. |
| 6,402,691 | B1 | 6/2002 | Peddicord et al. |
| 6,416,471 | B1 * | 7/2002 | Kumar et al. ............... 600/300 |
| 6,485,418 | B2 | 11/2002 | Yasushi et al. |
| 6,491,647 | B1 | 12/2002 | Bridger et al. |
| 6,501,386 | B2 | 12/2002 | Lehrman et al. |
| 6,516,289 | B2 | 2/2003 | David |

(Continued)

FOREIGN PATENT DOCUMENTS

WO WO 98/20439 5/1998

(Continued)

*Primary Examiner*—Donnie L Crosland
(74) *Attorney, Agent, or Firm*—Maier & Maier, PLLC (57) ABSTRACT

The present invention relates to a healthcare monitoring system and method that detects and transmits data. The system can utilize a wearable monitor that detects a variety of data from its wearer. The data can then be transmitted over a network to a centralized location where the data may be analyzed and any appropriate action may be taken.

32 Claims, 7 Drawing Sheets

U.S. PATENT DOCUMENTS

| | | | |
|---|---|---|---|
| 6,533,729 B1 | 3/2003 | Khair et al. | |
| 6,537,225 B1 | 3/2003 | Mills | |
| 6,540,673 B2 | 4/2003 | Gopinathan et al. | |
| 6,544,173 B2 * | 4/2003 | West et al. | 600/300 |
| 6,575,912 B1 | 6/2003 | Turcott | |
| 6,595,918 B2 | 7/2003 | Gopinathan et al. | |
| 6,608,562 B1 | 8/2003 | Kimura et al. | |
| 6,659,947 B1 * | 12/2003 | Carter et al. | 600/300 |
| 6,749,566 B2 * | 6/2004 | Russ | 600/300 |
| 6,864,796 B2 | 3/2005 | Lehrman et al. | |
| 6,921,367 B2 | 7/2005 | Mills | |
| 6,968,375 B1 | 11/2005 | Brown | |
| 7,053,767 B2 * | 5/2006 | Petite et al. | 340/531 |
| 2004/0111045 A1 | 6/2004 | Sullivan et al. | |
| 2006/0031934 A1 | 2/2006 | Kriegel | |

FOREIGN PATENT DOCUMENTS

| | | |
|---|---|---|
| WO | WO 03/008211 | 10/2003 |

\* cited by examiner

MOBILE WIRELESS CUSTOMIZABLE HEALTH AND CONDITION MONITOR

PRIORITY CLAIM UNDER 35 U.S.C. §119

This invention is related to and claims priority under 35 U.S.C. §119 to U.S. Provisional Patent Application No. 60/660,342, filed Mar. 11, 2005, the contents of which are hereby incorporated by reference in their entirety.

FIELD OF THE INVENTION

This invention relates to the field of health care monitoring and, more specifically, to the use of a wearable monitor to collect data on a patient and transmit the collected data to a centralized location with data storage, analysis, reporting and notification.

BACKGROUND

Nursing homes and assisted care facilities employ a number of different methods and devices to monitor their patients. These devices are capable of monitoring physiological functions, but are generally used in isolation and not integrated with other devices. Some devices include fall alert buttons that require a patient to actively push a button to alert the staff of a care facility of a fall. This type of device, however, is not effective for a patient who has a cognitive impairment (such as dementia) is knocked unconscious or otherwise rendered incapacitated by a fall or other medical condition. Care facilities also use a variety of pressure pads and other sensors to provide an audible alert to indicate that a patient has left a desired location. These types of devices have reliability problems and require a high level of vigilance to constantly monitor the sensors. Moreover, none of these devices is capable of delivering private, targeted and configurable alerts for designated caregivers, nor do they provide centralized data collection for automatic charting and close monitoring of individual patients.

In addition to the above, many care facilities try to perform at least some vital sign monitoring. This may be limited to checking a patient's vital signs only once a week due to the time and money needed to have staff to perform these duties. However, when a patient's vital signs are checked only once a week, the declining health of a patient may only be detected after a health condition has worsened, eliminating the opportunity for early intervention. Thus, there can be an increase in a care facility's patient morbidity and mortality rate. Additionally, staff turnover and productivity can be an issue in care facilities that may need to spend more time replacing and training staff members to monitor sensors and patients' vital signs and to understand the patient's medical history and specific need for care.

Care facilities also have an interest in knowing the location of their patients at their facility, as well as patients that may be located remotely or living at individual homes and receiving care remotely. However, typical methods of monitoring patients and determining their locations involve the use of video cameras and closed-circuit television. Another method is the use of motion detectors to infer movement and activity level within a home. These systems typically require significant wiring or installation of equipment within a home and can be uneconomical for either home or multi-patient facility use. Additionally, this may only provide an inference, but not a direct indication, of patient's well-being. Further, video-based services require a high level of attention to the video feeds from the cameras and the identity of the people can be difficult to discern. There are additional issues in personal privacy and intrusion when using video or even motion detectors. Additionally, it is not usually practical to have cameras or a video monitoring system in the house of a remotely located patient.

Other facilities, such as hospitals, have also utilized patient and personnel tracking systems using radio frequency identification (RFID) badges. These devices can be worn by a person and transmit an RF signal that may be tracked from a centralized location in the facility. These devices, however, do not provide any other information besides the location of the wearer and they may not provide adequate transmission range. Also, RFID is limited in its memory so very little processing is available and there is no 2-way processing of event monitoring data. Other information that a care facility may desire to collect, such as a patient's vital signs, are not collected or transmitted by these devices. Additionally, the battery life on these devices can vary significantly depending on the type of RF signal transmitted and the amount and duration of transmissions from the device. Typically the devices only have a battery life of a few days before they require recharging or replacing the batteries. Other devices designed to transmit a signal having information about a patient may utilize cellular phone technology. These devices, however, often fail to get an appropriate cellular signal in health care facilities and again require significantly more power and have a battery life of hours thereby rendering such devices impractical for long-term monitoring.

Yet other devices that have been used in battery-powered sensors include those using IEEE 802.15.1 Bluetooth wireless technology to replace cables. Enabling devices with Bluetooth does not in itself being about an integration of separate monitoring devices for one patient. Indeed, there can be a limit of eight devices that may be joined together in a Bluetooth piconet raising the question about supporting hundreds of patients in a facility. The short range, typically on the order of ten meters, calls for a multimode extensive network strategy to support a healthcare facility, such as a mesh or partial mesh network, would provide for adequate coverage but also exceeds the specifications of Bluetooth. Merely replacing a cable from a monitor to a wireless Bluetooth-enabled equivalent can result in rapid battery depletion if continuous monitoring is attempted.

Still other devices have been used for monitoring an individual's vital signs. These devices have been wearable and typically were capable of monitoring some vital signs, such as pulse rate and body temperature. These devices, however, typically only have the ability to display the information collected on a display that is either worn on the individual or on separate display that the collected data is downloaded onto. Other devices have included the ability to transmit location information to track the movement of an individual. These devices, however, do not have the ability to transmit collected data on the individual back to a central location for analysis. Further, these devices usually require a person to wear a variety of different sensors and can be intrusive on the person and prohibit some movement. These devices also only allow a person to wear the device for a limited time, for example a few days, before the power source must be replaced or recharged.

Therefore, a need exists for a system that can track and monitor a patient using a wearable, form-friendly, low-power, wireless device that can be used to monitor the health and wellness of a person wearing the device over long periods of time without the constant surveillance of healthcare personnel.

SUMMARY

In one embodiment, a system for monitoring a patient is disclosed. The system may have one or more wearable monitors that a person may wear. The one or more wearable monitors may have one or more sensors that collect data about the patient. The collected data may then be transmitted to at least one repeater, which passes the signal on to at least one gateway. The at least one gateway can transmit the collected data to at least one server for further analysis.

In another embodiment, a method of monitoring a person receiving health care is described. The method involves having a person wear a monitor with one or more sensors for collecting data from the wearer. The monitor can also be capable of transmitting data to a repeater. The repeater can then be used for transmitting data to a gateway, which in turn can be used for transmitting data over a local area network. Processing and interpreting the data can then be performed by a server.

In yet another embodiment, means for monitoring a health care patient are described. This may include means for collecting physiological data and other data from a person using a wearable device, means for transmitting the data to a centralized location and means for analyzing and interpreting the data.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Referring generally to FIGS. 1-6, a medical situation awareness system that can monitor the health, location or well-being of a person is shown. The system may include a user-friendly, internet-based interface and tools for analyzing data. The system may also include a scalable, customizable database for management and codification of the uncertain relational knowledge gathered. This database can include advanced analytic tools. Additionally, the system can include a Bayesian advanced analytic software tool that can take the uncertain relational knowledge gathered and develop a Bayesian relational network. This network may then be used to create a predictive model of medical condition for the monitored patient. The model may be used, for example, to filter false positives, incorrect data or inaccurate data. This autonomic process could allow for an effective wearable monitoring system because the event data from the sensors could require significant analysis time by an operator to ensure an accurate picture of the patient's overall health is provided. Further, the system may have a graphical interface that can be used for results analysis or health care suggestions. This system may be employed in any of a variety of situations, for example hospitals, extended care facilities, nursing homes, private homes, or any other situation where it is desirable to monitor and provide care for a person.

Figure 1:
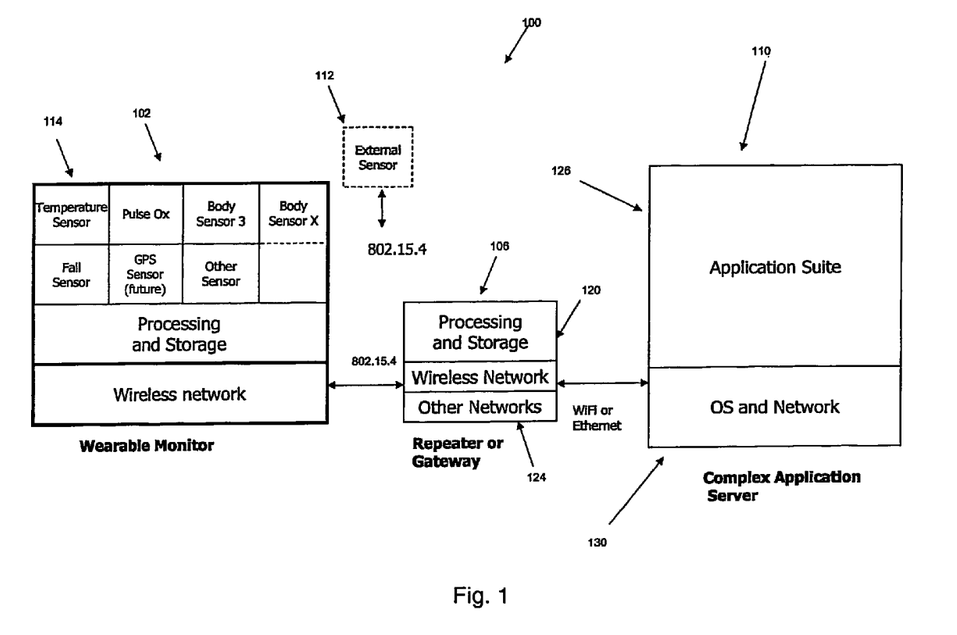
FIG. 1 shows an exemplary diagram of a health care monitoring system.

FIG. 1 shows an embodiment of a health care monitoring system. System 100 may have a variety of components, such as monitor 102, gateway 106 and server 110. Monitor 102, gateway 106, and server 110 may transmit data to each other and receive data from each other through any of a variety of wireless transmission protocols. Further, monitor 102 may include sensors 114 to detect physiological, locational and other data from a wearer of monitor 102. These sensors may include, but are not limited to a temperature sensor, a pulse oximetry sensor, a variety of body sensors, a fall detection sensor, and a location sensor, as well as any of a variety of other sensors. Additionally, external sensor 112 may be disposed separately from sensors 114 to detect and transmit data from a location apart from monitor 102. Monitor 102 may further include processing and storage capabilities 116 for processing and storing the data from the sensors as well as data received from outside sources. Also, mesh network 118 may be utilized with monitor 102. Mesh network 118 may include a variety of repeaters so as to allow for the transmission of data over significant areas as well as for use in providing location information of a wearer of monitor 102.

Gateway 106 can communicate wirelessly with monitor 102 and server 110 and may also include processing and storage capabilities 120, which may be able to process and store data transmitted from monitor 102, as well as data generated by gateway 106 and data received from server 110. Gateway 106 may be part of a wireless local area network (LAN) 122 and also part of other networks 124, allowing it to communicate with other devices, for example, over the Internet.

Server 110 may communicate with gateway 106 over network 130 to both send and receive data. Server 110 may include processing and storage capabilities 128, which may be used for processing, interpreting and storing data received from gateway 106 and monitor 102, as well as performing other analyses, such as eliminating false alarms and predicting future events. Further, server 110 can include a display 126, such as a nurse's display, where a person may access the data stored and processed by server 110.

Figure 1A:
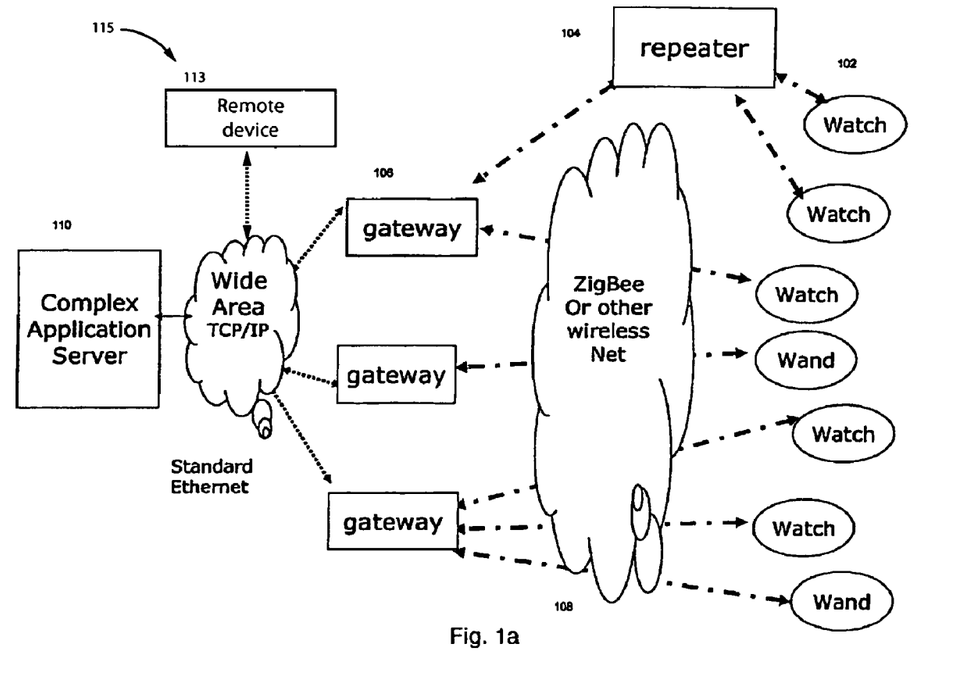
FIG. 1a shows an exemplary diagram of a health care monitoring system.

In another embodiment shown in FIG. 1a, a system 100 for monitoring the health, location or well-being of a person is shown. Here, a person may use a device such as a wearable monitor 102. The monitor 102 can be a hardware device taking the form of an arm band or a wrist band or a device that can be applied to the skin via a bandage, as a non-limiting example. In a further embodiment, the monitor 102 can be wearable and not interfere with any range of motion or actions of a person. The dimensions of the monitor 102 may also be small, for example, 1"×1"×3" or smaller. There may be a variety of sensors, such as a pulse sensor, temperature sensor and a mobility sensor, integrated into the monitor 102, as a few non-limiting examples. Further, a panic button may be disposed on the monitor 102, allowing a wearer or other person to send a signal to a remotely located party, such as a caregiver or a facility's server. Additionally, the monitor 102 may incorporate "fall detection," which can detect if a person falls down or otherwise moves in a manner that could result in an injury. The fall detection may use any of a variety of sensors, for example, piezoelectric-based, accelerometer-based and gyroscopic-based. The sensor or sensors may be incorporated in the monitor 102 whether it is worn on a wrist of a patient or anywhere else on their body. Further, the fall detection portion of the monitor 102 can send also send a signal to a caregiver or a facility's server.

In an additional embodiment of the monitoring system, the wearable monitor 102 can send a wireless signal to a repeater 104. The repeater 104 can be a custom hardware device that may be battery or AC powered. The repeater 104 may also be installed in any location where additional routing nodes may be required, to provide further wireless coverage and allowing the wearable monitor to communicate with a smart gateway.

Further, in the system shown in FIG. 1a, a smart gateway 106 may be utilized to further transmit a wireless signal. In one exemplary embodiment, the smart gateway 106 may be a hardware device that integrates IEEE 802.15.4 ZigBee wireless networking components with Ethernet, 802.11 wireless routers or a modem. IEEE 802.15.4 may be used as it allows a large number of nodes to join the network, thus permitting a large number of patients to be monitored. Communication may occur over the 2.4 GHZ band, which is unlicensed and available in most locations, allowing for a single product to be utilized throughout the world. Additionally, to avoid congestion caused by other devices using this band, the IEEE 802.15.4 ZigBee standard may use 16 channels in the 2.4 GHz band, allowing the monitor 102 to utilize less crowded channels when necessary. Likewise, any spectrum, such as the 5 GHz spectrum, may be used to avoid potential interference with other devices. Also, because 802.15.4 has a relatively long range, larger scale monitoring can occur. This transmission protocol is also a very low power protocol, allowing for extended use of the monitors, and the low data rate and limited interference with other devices allow for 802.15.4 devices to work in environments where other RF devices are already operating. However, in other exemplary embodiments, any other type of wireless networking devices, components or protocols may used with the gateway 106. The gateway 106 can collect the event data generated by the wearable monitor and may send real-time medical alerts directly to a caregiver or, alternatively, to a facility's server for further analysis and action.

Although the above embodiments discuss the IEEE 802.15.4 ZigBee wireless standard, any wireless communication protocol known by a person of ordinary skill in the art could be used for transmitting and receiving. In another embodiment, any wireless communication protocol known to a person having ordinary skill in the art that has economical power consumption, reasonable data rates, limited interferences, and sufficient range may be used.

After the wireless signal shown in FIG. 1a is transmitted from the smart gateway 106, it can pass through a local area network 108 to a server 110. The server 110 can be a software application that allows a nursing home facility or other care giving facility to track the incidence of fall reports, medical emergencies and other transmissions of the wearable monitor at their site. The server 110 can also have the ability to send targeted real-time medical alerts to facility employees and can escalate these alerts to various members on the staff, as well as track response times, for example, to the medical alerts. The server 110 may also provide statistics on the vital signs of the residents as well as the location of the residents. Further, the server 110 may be able to perform intelligent analyses of event data to minimize false alarms and allow for predictive decision support of healthcare providers, which could lead to improved care. Data transmitted to the server 110 may be forwarded to any of a variety of devices 113, and be viewable over the Internet or a local area network. The data may then be reviewed and analyzed by an authorized person at the remote location 115 of the device 113.

In yet another embodiment, the system 100 may be used in either a health care facility or at an individual's home. Further, a monitor 102 that functions in a health-care facility may also change locations to the individual's home or another location that is compatible with the system. Additionally, if the user moves back to the original care facility, the monitor 102 can continue to work seamlessly. Further, the same equipment for system 100 that is used in a health-care facility may be used for a patient at their home, as the equipment is typically relatively inexpensive. The message protocols used in the system can provide end-to-end integrity and security in the data from each wearable monitor and each sensor as the data is transmitted over wireless networks to the Internet or public carrier networks to reach the server having patient's records.

Figure 2:
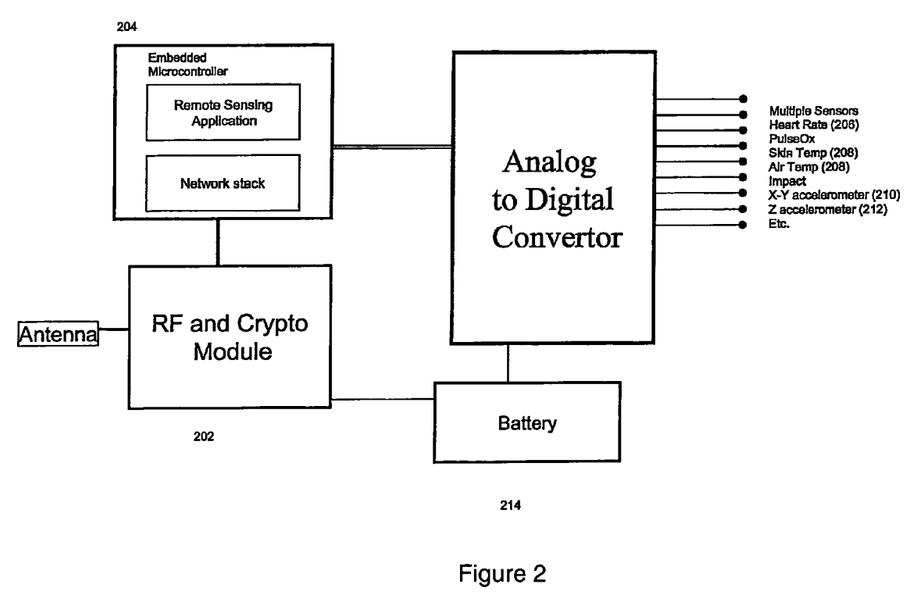
FIG. 2 shows an exemplary diagram of a wearable monitor.

FIG. 2 shows a more detailed diagram of the wearable monitor 102. The monitor 102 may be used to monitor the health and mobility of the wearer. In one embodiment, the monitor 102 may be a low-cost, high volume device that can be replaceable if it is lost or broken. The monitor 102 may also be customized based on whether or not it is being used in a wearer's home or at a care facility. The monitor 102 can include a wristband device, which may be a physically attractive, compact device capable of being worn on the wrist, similar to a wrist watch. Alternatively, the wearable monitor 102 may be a pager-sized device that can be attached to the belt of a wearer or to an armband or leg-band on the wearer. In yet another embodiment, the wearable monitor 102 could be formed so that it is integrated in a bandage or similar adhesive device that may be securely worn anywhere on the body of a wearer.

Although some embodiments have been described as including a wrist watch or pager-sized device, or the same divided into two or more smaller pieces, or any configuration known to one having ordinary skill in the art that would attach to the body securely and not inhibit or intrude upon the mobility, nor limit the range of motion of a user may be used. A version of the wearable monitor called a "wand" may be carried by authorized healthcare and support personnel. The wand can function to communicate with the server or other system components to verify patient identity, verify proper operation of the patient's wearable monitor, verify that the healthcare personnel have responded to medical alerts and notifications made by the system and have attended to the needs of the patient, as well as verify or determine any other relevant information.

The monitor 102 may have a variety of internal components, regardless of whether the wearer has the wristband device or the pager-sized device. An 802.15.4 wireless transceiver 202 may be disposed in the monitor. Alternatively, another wireless transceiver may be used with monitor 102. Additionally, an antenna can be disposed in the device. The antenna may be able to produce a significantly uniform signal having a significantly uniform signal strength emanating to all directions (substantially isotropic) regardless of the orientation of the monitor due to change in position of the wearer of the monitor. The antenna may further be optimized for communication in an indoor environment. A processor 204 may also be housed in the device. In an exemplary embodiment, the processor 204 can be an ultra-low power 8-bit processor. Additionally, a processor 204 may be utilized that has a hibernate mode where only micro-amps of current are used to power the hibernating device, and which only "wakes up" or activates to process events which can minimize power requirements and extend battery life. Flash memory (not pictured) may also be employed in the monitor 102. The flash memory can contain the latest sensor data and alerts when the wearable monitor is out of the range of a network, the protocol stack as well as firmware developed to react to events generated by the sensors.

In addition, the monitor can include any of a variety of sensors. These sensors can include medical-grade sensors which can be employed to determine the health of the wearer. For example, the sensors may include a pulse sensor 206, a temperature sensor 208 and accelerometers for the x-y axis 210 and z axis 212, allowing for mobility detection and fall detection. Further the mobile device can include a battery or batteries 214. The battery or batteries 214 may be such that they allow for the device to run off of the battery power for more than six months. Any of a variety of batteries may be used in both the wristband and pager-size applications.

Further embodiments of the monitor 102 not pictured in FIG. 2 may include a blood pressure sensor, a pulse oximetry sensor (to provide more accurate blood oxygen saturation determination mechanisms), a temperature sensor, respiratory rate sensor, wireless network-based location sensor and GPS or cell-based geo-location and E911 service. Individual sensors may be utilized to monitor these events or a single sensor may be utilized to perform a one or more of the tasks. Additionally, a shock meter that may use galvanic skin resistance and skin temperature, along with event analysis software to provide an early detection of shock may be incorporated.

Although the above preferred embodiments discuss a blood pressure sensor, laser pulse oximetry sensor, a temperature sensor, respiratory sensor, GPS and E911 services, any other sensor or service known to one having ordinary skill in the art may be used or incorporated into the device.

The wearable monitor 102 can use wireless networking components in order to send vital sign data, location information and medical emergency alerts. In one exemplary embodiment, 802.15.4 ZigBee wireless networking components (e.g. transceiver 202) may be used. In another exemplary embodiment, any other wireless networking components may be used that may be disposed on monitor 102 and provide for transmitting and receiving data wirelessly. Additionally, the monitor 102 can incorporate GPS locating capability to provide detailed location information of the wearer. Further, a cellular modem may be incorporated onto the monitor 102, allowing the wearer to be monitored from remote locations and, optionally, interacting with ZigBee or equivalent-enabled mobile phones.

The software that can be used in the wearable monitor 102 can be designed to be small, thus limiting the amount of processing power required and therefore extending battery life. Additionally, the software incorporated on the monitor 102 can be programmed into firmware. One portion of the software can include an IEEE 802.15.4/ZigBee protocol stack or any alternative wireless protocol stack. This combination can provide the ability for the wearable monitor 102 to wirelessly communicate with one or more repeaters and gateways. Additionally, in one embodiment, since the wearable monitor 102 may require very low power consumption, it can be considered an end node that does not route data, and thus may be considered a reduced function device (RFD) under the IEEE 802.15.4 standard. However, in other embodiments, the monitor 102 can have full routing functions and utilize any known wireless standard. Further, the software may also be able to respond to beacons from a gateway device that is requesting current sensor data to be sent. Also, in a further embodiment, the data transmitted from the wearable monitor 102 can be encrypted, for example, using the security capabilities of the 802.15.4 standard or any other Advanced Encryption Standard (i.e. AES 128) scheme known to one of ordinary skill in the art may be used.

Additional software may be used for processing sensor data and ensuring that out of range data is processed for all of the sensors that are integrated into the device. For example, in the case of fall detection, the software should be able to process the data and determine if a fall has occurred or if a typical movement has occurred. Also, sensor data may be gathered and sent to a gateway on a periodic basis for statistical tracking of norms. In a further embodiment, if there is a network failure, high-water mark sensor data can be latched and transmission can be retried until transmission is confirmed. Additionally, the wearable monitor 102 can also test battery power of battery 214 on a regular basis and may also transmit a "low battery" alert when battery life has decreased below a predetermined amount, for example, 20% of the remaining battery life. Alternatively, a "low battery" alert may be transmitted at any predetermined amount at or below 50% of the remaining battery life.

Figure 3:
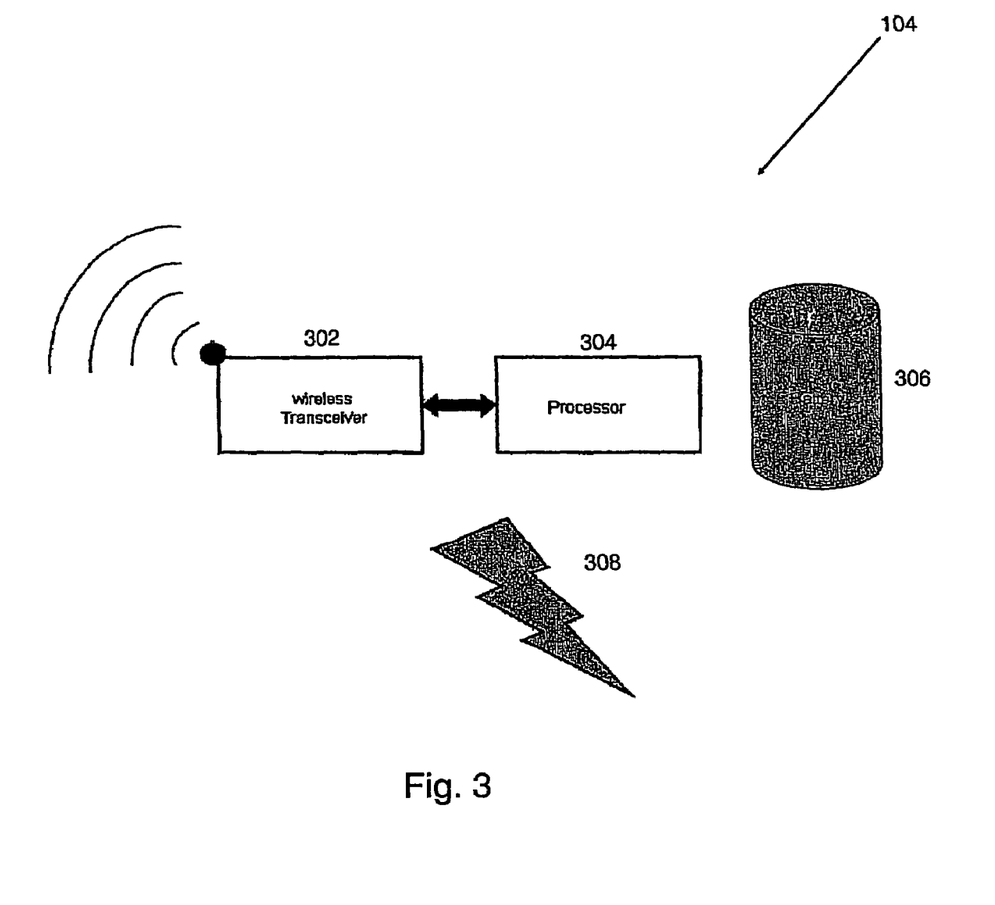
FIG. 3 shows an exemplary diagram of a repeater.

An exemplary repeater is shown in FIG. 3. A repeater 104 can ensure that adequate wireless coverage is maintained across the facility or home where the wearer of the monitor is located. In one embodiment, a repeater 104 can collect the statistics and alerts generated by the wearable monitor 102 and transmit real-time medical alerts to a caregiver or a care facility's server. Increasing the number of repeaters, for example in a mesh pattern or any other pattern known by one of ordinary skill in the art that will provide the desired coverage, in a given location, can also reduce the number of gateways that a home or facility may need. Additionally, the number of repeaters may be increased to support a virtually unlimited number of monitored patients and, additionally, determine the location of any individual patient. Repeaters can also compensate for the signal sent from an ultra-low power wearable monitor, which may have a limited transmission range. The repeater 104 can use a variety of hardware and software and may be changed or customized depending on the type of repeater that is being used. Non-limiting examples of different repeaters include an internal-use-only repeater that is A/C powered with battery backup, an internal-use-only repeater that is D/C battery powered, a weatherproof repeater that is A/C powered with battery backup, and a weatherproof repeater that is D/C battery powered.

A repeater 104 may also utilize a variety of internal hardware components, as shown in FIG. 3. With the exception of the A/C power transformer in the A/C power devices, the hardware configurations for different repeaters may all be the same. The repeater can house an 802.15.4 wireless transceiver 302 that meets both the size and power requirements of the device. The 802.15.4 transceiver 302 may be further integrated with an Ethernet connection, one or more 802.11 wireless Internet routers and one or more dial-up modems (not shown). In other embodiments, the repeater 104 may house any other type of wireless transceiver. Additionally, the repeater 104 can have an antenna, which may be customized or altered depending on whether or not the monitor is being used indoors or outdoors. Further, the repeater 104 may also have an ultra-low power 8-bit processor 304, similar to the one described above with respect to the monitor and optionally having a hibernate mode. Additionally, the repeater 104 can utilize flash memory containing the protocol stack as well as firmware developed to react to repeater events, a battery or batteries 306, which may power the repeater for one year or longer and an A/C power transformer 308, which can be utilized for locations with an electrical plug.

The repeater 104 may also have a software component designed to be small to limit the amount of processing power and thus extending the battery 306 life in the event that the device is not A/C powered. This software may be entirely programmed into the firmware. One part of the software may be the IEEE 802.15.4/ZigBee protocol stack, or any other appropriate wireless protocol stack, which can provide the ability for the repeater to wirelessly communicate with wearable monitors and gateways in the system. The repeater 104 can be designed as a routing node, allowing it to pass data along from source nodes to destination nodes. The repeater may also be considered a full function device (FFD) in terms of the IEEE 802.15.4 standard. The repeater 104 further may utilize any of a variety of batteries, for example M batteries, to power it as it routes data or may alternatively be A/C powered. Finally, the software on the repeater 104 may also respond to beacons from a gateway device, which can request current status to be sent. The status data transmitted from the repeater 104 to a gateway device can include both status data of the repeater 104 itself as well as current status data of the wearer of the monitor 102. If the repeater 104 is battery powered, additional processing may be performed that tests the battery power on a regular basis and sends a low battery alert when a predetermined amount of battery power in battery or batteries 306 is, for example 20%. Alternatively, a "low battery" alert may be transmitted at any predetermined amount at or below 50% of the remaining battery life.

Figure 4:
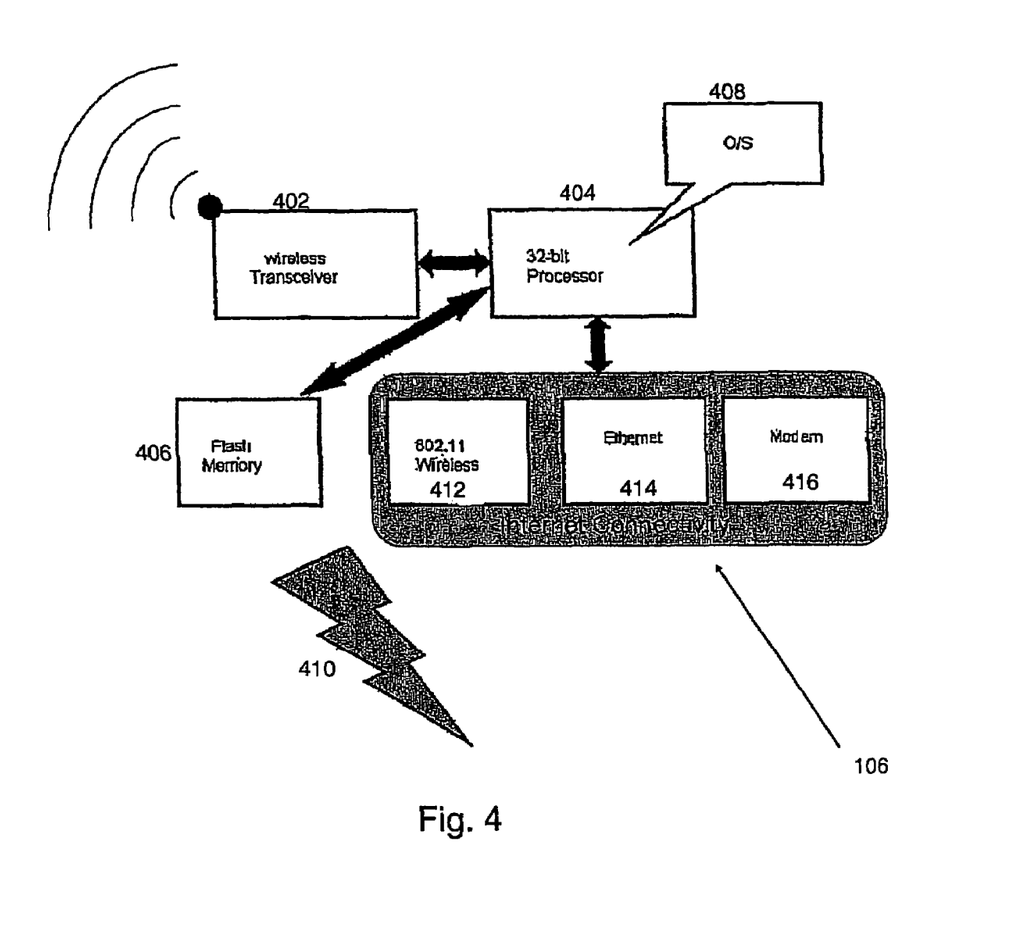
FIG. 4 shows an exemplary diagram of a gateway.

An exemplary gateway device, as shown in FIG. 1, item 106, is shown in greater detail in FIG. 4. The gateway device 106 can be a fixed-location device that bridges a 802.15.4 ZigBee wireless network, or any other alternative wireless network used by the above-described devices, with a local area network in a facility or home. A variety of wearable monitors 102 and repeaters 104 may operate through an individual gateway 106 and the gateway 106 may have similar functionality to an 802.11 wireless access point, or any other type of wireless access point. Similar to the repeater 104, the gateway 106 may utilize a variety of hardware and software components. Additionally, the gateway 106 may have different configuration based on the local area network 108 that is configured in a facility or home. For example, a gateway 106 may be an A/C powered device with Ethernet network connectivity, an A/C powered device with 802.11b (or other) network connectivity, or an A/C powered device with modem connectivity.

In a further embodiment shown in FIG. 4, a gateway 106 may have a variety of hardware components. These components may include an 802.15.4 wireless transceiver 402, or any other type of wireless transceiver, and an antenna, similar to those in the repeater 104. The gateway 106 may also have a processor 404, for example a 32-bit processor. Additionally, the gateway 106 can utilize flash memory 406, or other memory type, which can store patient data as a temporary network buffer and contain the protocol stack as well as firmware message processing 408. The gateway 106 can also have an amount of RAM that is needed for the application and an A/C power transformer 410 to provide power for the gateway, as well as an internal D/C battery backup.

The gateway 106 may also provide Internet connectivity. Connections to the Internet may be made by at least one of an 802.11 wireless connection 412, Ethernet connection 414 or modem 416, or any other device capable of connecting to the Internet.

The software used in the gateway 106 shown in FIG. 4 can be used in processing events from the wearable monitor and may optionally be Linux-based. Additionally, all of the software incorporated into the gateway may be programmed into the firmware. One such software component is an operating system, for example a Linux or Linux-variant operating system 408. Further, the gateway 106 can include an IEEE 802.15.4/ZigBee protocol stack, or any other type of wireless protocol stack, the combination of which can provide the ability for the gateway 106 to wirelessly communicate with wearable monitors 102 and repeaters 104 in the system 100. The gateway 106 may further be designed as a routing node so that it can pass data along from source nodes to destination nodes. The gateway 106 may be considered a personal area network (PAN) coordinator node under the terms of the IEEE 802.15.4 or master node under IEEE 802.15.1 or other wireless standard. Additionally, if there are multiple gateways in the network for scalability, a single gateway may be chosen as the PAN coordinator and the remaining gateways can function as coordinators in a cluster tree network topology. The coordinator nodes can also generate beacons, for example status requests, that the other nodes in the network may respond to on a periodic basis.

Other software included in a gateway 106 can include a reliable queue, which can provide for scalability and reliability of the delivery of critical monitoring events to the server. A gateway 106 can also have the capability to process the events sent to it by the wearable monitors 102 and the repeaters 104. In situations where there may be multiple events from the same monitor 102 or repeater 104, the gateway 106 can have the intelligence to collapse the events and perform a root cause analysis. Finally, gateways can receive software upgrades and updates. Further, gateways may be able to upgrade the wearable monitor and repeater components when new firmware is made available for updates.

In another embodiment, the system may be utilized in the home of a patient. A home-based system, however, may contain a gateway 106 having additional intelligence so that it also can have the decision making capabilities based on a patient's physiological trends and statistical data for instances where a patient can be provided immediate feedback for self awareness and patient education about their ailments. The gateway device 106 may also be able to continue communication with a healthcare provider's server 110 so that a healthcare team can maintain their ability to monitor the patient. The communication between the system in the patient's home and the healthcare facility can be securely delivered through encryption to ensure patient privacy and, if necessary, to comply with the Health Insurance Portability and Accountability Act (HIPAA) regulations and, if necessary, military specific requirements.

Figure 5:
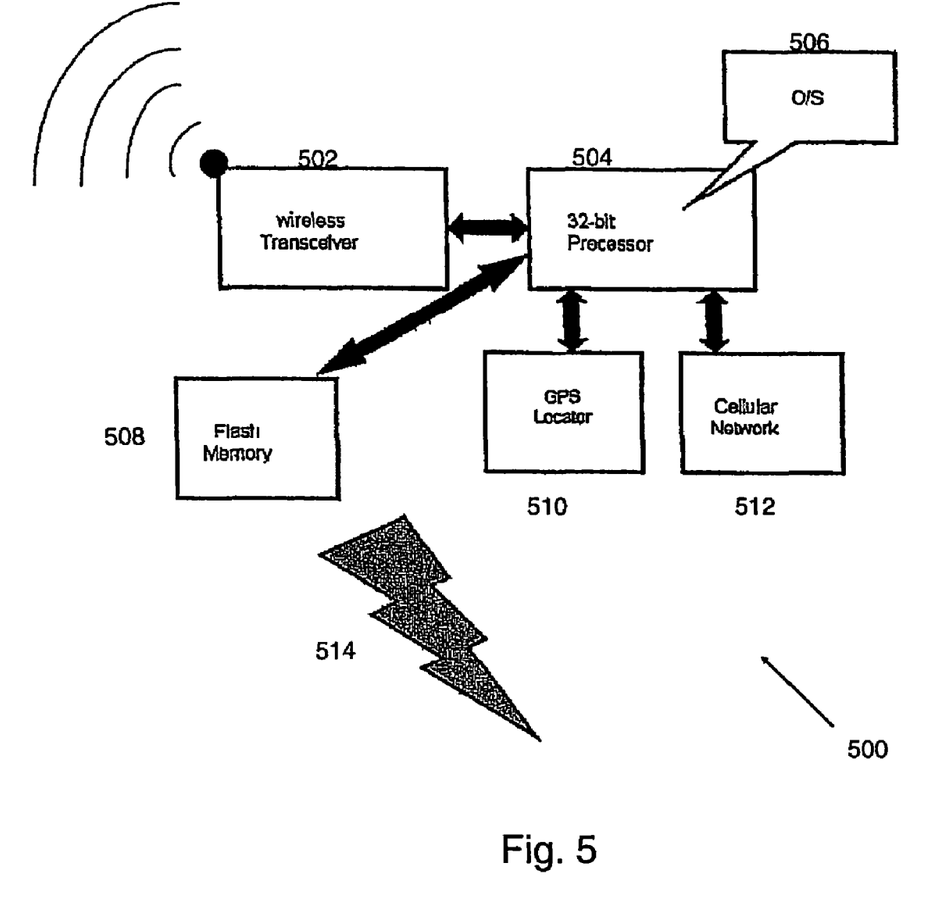
FIG. 5 shows an exemplary diagram of a mobile gateway.

In an alternative embodiment shown in FIG. 5, a mobile gateway 500 may be used in lieu of or with gateway 106. The mobile gateway 500 functions similarly to gateway 106, insofar as it can have a wireless transceiver 502 and antenna, processor 504, operating system 506 and flash memory 508. A mobile gateway 500 can also bridge the ZigBee wireless network, or any other wireless network used with the system, with a cellular network 512 and allow for monitoring of the wearer of a monitor 102 when the monitor 102 is away from their home or facility. A mobile gateway 500 can also contain GPS locator 510 capabilities to identify the location of the wearer in case of an emergency event. Further, mobile gateway 500 may use rechargeable battery 514 to power the device. A mobile gateway 500 may be configured in a variety of manners, such as by partnering with a mobile phone manufacturer to integrate gateway capabilities into a ZigBee-enabled, or other wireless protocol-enabled, mobile phone or by integrating gateway cellular and GPS capabilities into a wearable monitor.

Figure 6:
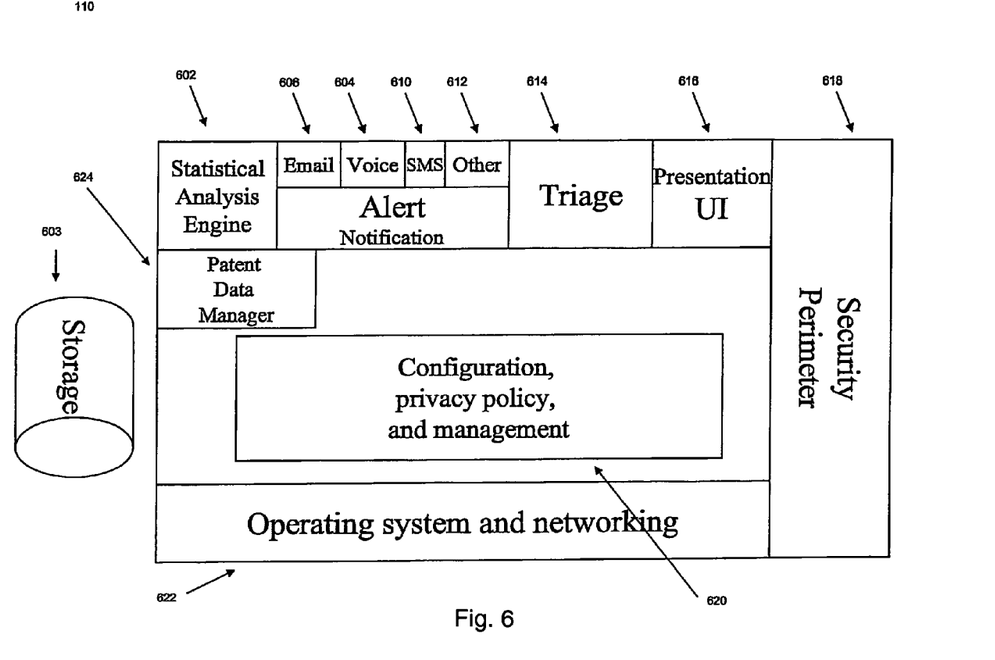
FIG. 6 shows an exemplary diagram of a server.

FIG. 6 shows a more detailed view of server 110. The server 110 can process the logic associated with the monitoring system 100 and provide the capability to configure the user information and handle the processing of events from various users using statistical analysis engine 602. Further, the server 110 can track and store the incidence of falls and other medical emergencies at the site using storage, database or databases, or memory 603 in conjunction with statistical analysis engine 602. It can also have the ability to send targeted real-time medical alerts to caregivers and may optionally escalate these alerts to additional members of a healthcare team as well as track response times using alert notification 604. These alerts may include email 606, voice transmission 608, SMS 610 or other alert transmission 612. The server 110 may also provide statistics on the vital signs of a patient or patients as well as their location and, through the use of complex applications software, can make intelligent decisions based on trends in patient data and statistical data using tools disposed in statistical analysis engine 602. Server 110 may include triage sorting capabilities 614, allowing for improved organization of patient data. A presentation user interface 616 may also be used with server 110 so as to provide an accessible and easily navigable way of viewing data in server 110. The presentation user interface 616 further be used by operating system and networking software 622 to provide additional methods of user access. Additionally, server 110 may have security perimeter 618, which may prevent unauthorized access to data transmitted to the server. Network configuration data, privacy information and management data 620 may also be housed on server 110. Finally, server 110 may also include patient data manager 624, which may house any of a variety of data associated with any number of patients.

The server 110 may also include one or more databases 603. Data stored in the one or more databases 603 can include accumulated patient information and system configuration information. This information can be used for a variety of purposes, such as supporting one or more remote monitors, one or gateways, one or more repeaters, and any other device that may be used in the system.

In one exemplary embodiment, at least one server may be used for deployment in support of a number of gateways, repeaters and monitors. The server, e.g. server 110, and system architecture can be flexible and scalable, however, allowing the number of servers deployed will be determined, for example, by the unique requirements presented by institutional organization, the desire by the institution for local or remote maintenance support, physical and geographic distance, network reliability, desired separation of data among multiple institutions, processing capacity desired and any other relevant needs or desires. Processing may be distributed across multiple specialized servers, which can allow, for example, certain portions of the database and complex software applications for statistics to be on one or more servers at one location, and certain portions of the database and complex software applications for communications and configuration with gateways and associated repeaters and monitors might be at another location or locations. Some deployments may include gateways, repeaters and monitors at one location but all of its supporting servers are at a different location.

The server 110 may include software bundles with rack-mounted server hardware included in operating system and networking software 622. This can be, for example, a standard Intel-based processor and PC-like functionality. Further, the server 110 associated with a deployment can have a variety of application software built on top of open source software components. Other software components can include an operating system, such as Linux, a Linux variant, Windows or a Windows-based operating system. A web-based interface, such as presentation interface 616, can also be provided via a web server, for example Apache http server. Further, an application server, such as Tomcat, can be used to dynamically monitor events and statistics and configure contact information notification services. A database may also be used to persist the configuration and data, such as patient information, contact data, and statistics. Because multiple patients, multiple monitors and multiple sensors may be included in the system, the configuration may have unique identifiers for each patient, as stored in patient data manager 624. Additionally, a set of unique messages appropriate for each type of event and each type of data from a sensor may be used. Complex software applications, such as engine 602, may utilize the data to create patient records, statistics, and analysis of data for reports. Complex software applications can also apply statistical techniques such as Bayesian Networks, moving averages, regression analysis, inference, probabilistic reasoning, and other analytical, machine learning, and artificial intelligence techniques known to a person having ordinary skill in the art to filter and apply data. Standard reports can be available on a per-event, per-patient, and per-facility basis, as well as any other desired basis. The ability to customize reports can be made available and the output from these reports could potentially also be used for billing or for quality control. Examples of open-source database projects that may be utilized are Apache projects such as Apache Derby, and mySQL or other databases known to a person having ordinary skill in the art.

The server 110 software may also include reliable queue, which can ensure scalability and reliability of the delivery of critical monitoring events to the caregiver mobile devices. Additionally, a notification service can provide the ability to communicate with mobile devices as well as the ability to send SMS text messages to pages and mobile phones as well as the sending of voice messages. The server 110 can further have the ability to process all of the events sent to it by the gateways in the facility or network and, additionally, the server 110 can have the ability to upgrade the gateway 106 as well as provide firmware to the gateway 106, which, in turn, can upgrade the wearable monitor 102 and repeater 104 components when new firmware, if desired, is available.

In another exemplary embodiment, server 110 may be able to identify specific sensor values and time stamps that originate from a specific monitor, e.g. monitor 102. This identification may be able to take place regardless of how the data from monitor 102 is transmitted or over which network path or paths the data is transmitted. For example, server 110 may identify data as being sourced from monitor 102 despite the data generated by monitor 102 having traveled over one or more of a wireless network, the Internet, a private local area network (LAN), wide area network (WAN), and a satellite or public carrier wired or wireless network. Additionally, server 110 may also account for data that may have been temporarily stored in monitor 102 when transmission was not available and later transmitted to server 110. The data sent from an exemplary monitor may include a protocol of identification and unique or specific messages and formats for the exemplary monitor. The transmitted data may include information such as values generated by sensors disposed on the monitor, the time of a sensor value, information supportive of a message error detection and correction scheme and an encryption method to protect user privacy, which may exceed HIPAA standards.

In another embodiment, server 110 may provide notification or report information on the wellness or health of a wearer of monitor 102. Server 110 may provide this information by utilizing complex application software that compares incoming data from monitor 102 with previously stored data from monitor 102 and other monitors recording similar data. The comparison of the sum of the data can be used to generate predictive probabilistic statistics, for example probabilistic statistics derived from Bayesian inference networks and probabilistic relations with a deterministic predictive capability for impending events. The data sourced from monitor 102 may be further be encrypted and server 110 may decrypt the data prior to processing and analyzing it. This data may also be correlated to generate notifications indicating changes in the health status of a wearer of monitor 102. Additionally, server 110 may generate location data for monitor 102 based on the network interaction and signal attributes of monitor 102, such as which devices monitor 102 is transmitting to and which network paths data generated by monitor 102 are being transmitted over.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed:

1. A monitoring system, comprising:
   at least one wearable monitor having a transceiver, a microprocessor, memory and at least one sensor;
   at least one gateway having a transceiver;
   at least one device located at a remote location; and
   at least one server coupled in communication using a wide area network to the at least one gateway and the at least one device;
   the at least one sensor in the at least one wearable monitor sensing data from a wearer of the at least one wearable monitor and transmitting the data to the at least one gateway, and the at least one gateway transmitting the data to the at least one server, wherein the server analyzes the data in real-time for current and predicted future health problems of the wearer, generates health problem alerts and sends the health problem alerts to a caregiver.

2. The monitoring system as in claim 1, wherein the at least one wearable monitor has an IEEE 802.15.4 transceiver.

3. The monitoring system as in claim 1, wherein the at least one sensor of the at least one wearable monitor detects at least one of physiological data, location and status of a person.

4. The monitoring system as in claim 1, wherein the at least one sensor includes a pulse sensor, a temperature sensor and an accelerometer.

5. The monitoring system as in claim 1, wherein the at least one wearable monitor can operate continuously for six to 12 months using at least one battery.

6. The monitoring system as in claim 1, wherein the at least one sensor includes an accelerometer that determines whether or not a wearer of the at least one wearable monitor has fallen down.

7. The monitoring system as in claim 1, wherein the at least one wearable monitor has a processor.

8. The monitoring system as in claim 1, further comprising at least one repeater, wherein the at least one repeater is used to transmit data to and receive data from the at least one wearable monitor and the at least one gateway, and provides location information of a wearer of the wearable monitoring system to the at least one gateway.

9. The monitoring system as in claim 1, wherein the wearable monitor has at least one accelerometer that detects when a person wearing the wearable monitor falls down.

10. The monitoring system as in claim 1, wherein the at least one server has at least one database containing accumulated patient information and system configuration information to support one or more remote monitors, gateways or repeaters.

11. The monitoring system as in claim 1, wherein the at least one server has application software to calculate statistics from data incidental to the operation of the system, using statistical methodologies to make determinations about the current health condition of the user and to make predictive probabilistic determinations about future outcomes.

12. The monitoring system as in claim 1, wherein the at least one server sends the health problem alerts to a mobile device of the caregiver.

13. A method of healthcare monitoring, comprising:
   sensing data on a person using a wearable monitoring device;
   transmitting data to at least one gateway and at least one server;
   analyzing the data at the at least one server;
   determining a current and predicted future health problems of the person;
   sending the analyzed data using a wide area network to at least one device located at a remote location;
   acting on the analyzed data; and
   sending alerts of at least one of the current and predicted future health problems of the person to a caregiver of the person.

14. The method of healthcare monitoring as in claim 13, wherein the data sensed on the person using the wearable monitoring device is at least one of physiological data, location data, mobility, and movement.

15. The method of healthcare monitoring as in claim 13, wherein the data sensed on the person is transmitted by the wearable monitoring device using the IEEE 802.15.4 transmission protocol.

16. The method of healthcare monitoring as in claim 13, further comprising:
   updating the software housed in the wearable monitoring device and at least one gateway may be updated by instructions transmitted from the at least one server.

17. The method of healthcare monitoring as in claim 10, wherein the wearable device is worn on a wrist.

18. The method of healthcare monitoring as in claim 13, wherein the wearable device comprises at least one piece that can be attached to the clothing of a user.

19. The method of healthcare monitoring as in claim 13, wherein the server monitors and processes events and statistics with complex applications of statistical software analyzing patient information in databases and supporting standard and customized reports.

20. The method of healthcare monitoring as in claim 13, further comprising:

detecting when a person falls with accelerometers disposed in the wearable device.

21. The method of healthcare monitoring as in claim 13, wherein the at least one server can identify from a large active population a wearable device from which data is transmitted over numerous networks, decrypt any encrypted data transmitted from the wearable device, determine the type of data generated by sensors disposed on the wearable device, determine the time the data was generated by the wearable device, and determine the time the data was transmitted by the wearable device.

22. The method of healthcare monitoring as in claim 13, wherein the wearable monitoring device and at least one gateway are battery powered.

23. The method of healthcare monitoring as in claim 13, wherein the at least one server provides notifications and reports on user wellness using application software to compare incoming and stored sensor data from the wearable device and their statistics against predictive probabilistic statistics.

24. The method of healthcare monitoring as in claim 13, wherein one or more sensors disposed on the wearable device take periodic samples of data, the frequency of sample taking and recording in a database being controlled by at least one of the occurrence of an event, sensing data having a value exceeding a pre-determined value and a probabilistic determination made by a statistics calculation.

25. The method of healthcare monitoring as in claim 13, wherein the data transmitted over the system is encrypted.

26. The method of healthcare monitoring as in claim 13, wherein real time data collected from two or more sensors disposed on the wearable device are correlated to determine notifications and changes in health status of a wearer.

27. The method of healthcare monitoring as in claim 13, wherein data collected from one or more sensors disposed on the wearable device are grouped into probabilistic relations with a deterministic predictive capability for impending events.

28. The method of healthcare monitoring as in claim 13, wherein the location of a wearer of the wearable device can be determined using at least one of network interaction and signal attributes.

29. The method of healthcare monitoring as in claim 28, wherein an antenna disposed on the wearable device produces significantly uniform signal strength in any direction.

30. The healthcare monitoring system of claim 24, further comprising means for continuously powering the wearable device for at least six months.

31. The method of healthcare monitoring as in claim 13, further comprising sending alerts of at least one of the current and future health problems of the person to a mobile device of the caregiver of the person.

32. A healthcare monitoring system, comprising:

means for sensing physiological data of a patient wearing a wearable device;
means for transmitting the data to a series of network devices;
means for receiving the data at a centralized location;
means for determining a current and predicted future health problems of the patient;
means for analyzing the data at the centralized location;
means for transmitting the analyzed data over a wide area network to at least one remote device; and
means for sending health problem alerts to a caregiver of the patient.

* * * * *